US005360730A

United States Patent [19]
Orndorff et al.

[11] Patent Number: 5,360,730
[45] Date of Patent: * Nov. 1, 1994

[54] ZEAXANTHIN PRODUCING STRAINS OF NEOSPONGIOCOCCUM EXCENTRICUM

[75] Inventors: Steve A. Orndorff, Arvada; Elizabeth A. Campbell, Evans; Richard D. Medwid, Fort Collins, all of Colo.

[73] Assignee: Universal Foods Corporation, Milwaukee, Wis.

[*] Notice: The portion of the term of this patent subsequent to Sep. 27, 2016 has been disclaimed.

[21] Appl. No.: 776,665

[22] Filed: Oct. 15, 1991

Related U.S. Application Data

[63] Continuation-in-part of Ser. No. 524,140, May 15, 1990, abandoned, and a continuation-in-part of Ser. No. 474,248, Feb. 5, 1990, abandoned, which is a continuation of Ser. No. 58,512, Jun. 5, 1987, abandoned.

[51] Int. Cl.$^5$ ............... C12N 1/12; C12P 23/00
[52] U.S. Cl. .................. 435/257.1; 435/67; 435/172.1; 47/1.4
[58] Field of Search ............ 435/257.1, 172.1, 67; 47/1.4

[56] References Cited

U.S. PATENT DOCUMENTS

| | | | |
|---|---|---|---|
| 2,949,700 | 4/1960 | Kathrein | 435/67 |
| 2,974,044 | 3/1961 | Farrow et al. | 435/67 |
| 3,108,402 | 10/1963 | Kathrein | 435/67 |
| 3,206,316 | 9/1965 | Klaul | 435/67 |
| 3,280,502 | 10/1966 | Farrow et al. | 435/67 |
| 3,539,686 | 11/1970 | Rosenberg | 435/67 |
| 3,681,082 | 8/1972 | Schwieter et al. | 435/67 |
| 3,841,967 | 10/1974 | Dasek et al. | 435/67 |
| 3,891,504 | 6/1975 | Schocher et al. | 435/67 |
| 3,951,742 | 4/1976 | Shepherd et al. | 435/67 |
| 3,951,743 | 4/1976 | Shepherd et al. | 435/67 |

FOREIGN PATENT DOCUMENTS

| | | |
|---|---|---|
| 0393690 | 10/1990 | European Pat. Off. |
| WO91/03571 | 3/1991 | European Pat. Off. |
| 1071636 | 2/1984 | U.S.S.R. |

OTHER PUBLICATIONS

Moore, et al., "The Role of Carotenoids in Preventing Oxidative Damage in the Pigmented Yeast, *Rhodotorula mucilaginosa*", *Archives of Biochemistry and Biophysics*, vol. 270(2), pp. 419–431 (1989).

Krinsky, "Antioxidant Functions of Carotenoids", *Free Radical Biology and Medicine*, vol. 7, pp. 617–635 (1989).

Nelis and Leenheer, "Microbial Sources of Carotenoid Pigments Used in Foods and Feed", *Journal of Applied Bacteriology*, vol. 70, pp. 181–191 (1991).

Marusich, "Zeaxanthin as a Broiler Pigmenter", *Poultry Science*, vol. 55, pp. 1486–1494 (1976).

"Algae–Derived Xanthophylls for Pigmentation Control", *Feeds Illustrated*, vol. 13, pp. 24–25, Nov. (1962).

Spurgeon, et al., "Carotenoids", *The Biochemistry of Plants*, vol. 4, pp. 419–469 (1980).

Marusich, et al., "Oxycarotenoids in Poultry Pigmentation", *Poultry Science*, vol. 49(6), pp. 1555–1566 (1970).

Urbach, et al., "Effect of Substituted Pyridazione Herbicides and of Difunone (EMD-IT 5914) On Carotenoids in Biosynthesis in Green Algae", *Naturforsch*, vol. 31cZ., pp. 265-55 (1976).

Van Nostrand's Scientific Encyclopedia, pp. 79–84 (Van Nostrand Rheinhold Co. 6th Ed. 1983).

(List continued on next page.)

*Primary Examiner*—Irene Marx
*Attorney, Agent, or Firm*—Whyte Hirschboeck Dudek

[57] ABSTRACT

The present invention is directed toward a process for producing zeaxanthin which includes mutating algal microorganisms, selecting from said mutated microorganisms a microorganism capable of producing zeaxanthin, culturing the selected microorganism in an effective medium to produce zeaxanthin, and recovering zeaxanthin produced by the selected microorganism. The present invention also provides microorganisms capable of producing zeaxanthin, formulations containing zeaxanthin produced by the disclosed process and the use of such formulations to enhance pigmentation and to reduce damage caused by reactive oxygen species and phototoxic molecules.

2 Claims, No Drawings

OTHER PUBLICATIONS

Deason, "The Genera Spongiococcum and Neospongiococcum. I. The Genus Neospongiococcum and the Multi-Nucliate Spieces of the Genus Neospongiococcum", *Phycologia* 10(1) pp. 17–27 (1971).

Deason, "The Genera Spongiococcum and Neospongiococcum. II. Species of Neospongiococcum with Labile Walls", *Phycologia* 10(2–3), pp. 255–262 (1971).

Deason, "The Genera Spongiococcum and Neospongiococcum. (Chlorophycea, Chlorococcales) III. New Species, Biochemical Characteristics and A Summary Key", *Phycologia* 15(2), pp. 197–213 (1976).

Deason, "Taxonomic Significance of Secondary Carotenoid Formation in Neospongiococcum", *J. Phycol.* 13, pp. 176–180 (1977).

Deason, "Mitosis and Cleavage During Zoosporogenesis in Several Coccoid Green Algae", *J. Phycol.* 15, pp. 371–378 (1979).

Parker, et al., "Facultative Heterotrophy in Some Chlorococcasean Algae" *Science,* vol. 133, pp. 761–763 (1961).

Khadke, et al., "The Physiology of Neospongiococcum Ovatum Deason", *New Phytol.*, vol. 77, pp. 635–639 (1976).

Sylvester, et al., "Dark and Light Grown Algal Species of the Genus Neospongiococcum", *Proceedings of the Pennsylvania Academy of Science,* vol. 49(2), pp. 129–134 (1975).

Bailey and Ollis, "Kinetics of Substrate Utilization, Product Formation, and Biomass Production in Cell Cultures", *Biochemical Engineering Fundamentals,* ch. 7, pp. 373–456 (McGraw Hill 2d. ed. 1986).

Theriault, "Heterotrophic Growth and Production of Xanthophylls by *Chorella Pyrenoidosa*", *Appl. Microbiol.,* vol. 13(3), pp. 402–416 (1965).

Bold, *Morphology of Plants,* p. 39 (Harper and Row, Inc., New York 1967).

Ben–Amotz, et al., *Ann. Rev. Microbiol.,* vol. 37, p. 112 in particular, (1983).

Droop, "Algae", *Methods in Microbiology,* vol. 3B., ch. XI, pp. 286–299 (Academic Press, N.Y., J. R. Norris et al. eds. 1969).

Kuzmicky, et al., "Pigmentation Potency of Xanthophyll Sources" *CRC Handbook of Microalgal Mass Culture,* pp. 339–419 (A. Richmond ed. 1986).

Vaisberg, et al., "Events Surrounding the Early Development of Euglena Chloroplasts. 7. Inhibition of Carotenoid Biosynthesis by the Herbicide SAN 9789 [formula] and its Developmental Consequences", *Plant Physiol.,* vol. 57(2), pp. 260–269 (1976).

Gombos et al, *Plant Physiol.,* vol. 80(2), pp. 415–419, 1980.

Young et al, *Photosynth. Res,* 25(2), 129–136, 1990.

Hager et al., *Archmikrobiol.,* 72(1), 68–83, 1970.

Brown et al, *Phycologia,* 21(1), pp. 9–16, 1982.

Czeczaga et al, *Biochem. Syst. E col.,* vol. 15 (1), pp. 5–8, 1986.

Sikyta, B, "Methods in Industrial Microbiology", 1983, pp. 214–215.

Hager et al., *Planta,* vol. 76 (2), pp. 138–148, 1967.

Kleinig, H, *Planta,* vol. 75 (1), pp. 73–76, 1967.

Hunter et al., *Proc. Pa Acad Sci,* vol. 52 (1) 1978, p. 105.

ZEAXANTHIN PRODUCING STRAINS OF *NEOSPONGIOCOCCUM EXCENTRICUM*

This is a continuation-in-part of U.S. Pat. application Ser. No. 07/524,140, filed May 15, 1990, now abandoned, entitled "A High Productivity, Continuous Fermentation Process for Carotenoid-Producing Microorganisms," which is incorporated herein by reference in its entirety. This is also a continuation-in-part of U.S. Pat. application Ser. No. 07/474,248, filed Feb. 5, 1990, now abandoned, entitled "Carotenoid Producing Culture Using *Neospongiococcum Excentricum*," which is incorporated herein by reference in its entirety and which is a Continuation Application of U.S. Pat. application Ser. No. 07/058,512, filed Jun. 5, 1987, now abandoned, entitled "Carotenoid Producing Strains of Microorganisms and Methods for Selecting."

FIELD OF THE INVENTION

Field of the Invention

The present invention provides a process for producing zeaxanthin which includes a process for producing microorganisms capable of producing zeaxanthin as well as the microorganisms produced thereby. The present invention further provides formulations containing zeaxanthin produced by the disclosed process and the use of such formulations to enhance pigmentation and to reduce damage caused by reactive oxygen species and phototoxic molecules.

BACKGROUND OF THE INVENTION

Zeaxanthin, or 3,3'-dihydroxy-beta-carotene, is a natural carotenoid alcohol useful in the pigmentation of foodstuffs and cosmetics. For example, zeaxanthin imparts a desirable yellow to reddish-yellow color to the flesh, skin, and eggs of poultry and fish. Zeaxanthin is more desirable as a food dye than are chemically synthesized dyes, many of which have been banned by governmental agencies due to their mutagenic and carcinogenic potential. Natural carotenoids, which apparently have no toxic effects even at high concentrations, may replace yellow and red azo dyes that have proven to be harmful to animals.

Some carotenoids, such as zeaxanthin, are effective antioxidants due to their conjugated diene chemical structures. Thus, zeaxanthin may also be used to reduce damage to tissues caused by oxygen-free radicals, to prevent certain types of cancer, and to stabilize compounds subject to oxidation, particularly when exposed to light.

Zeaxanthin is preferred over other carotenoids for enhancing pigmentation in poultry and fish due to its potency, ability to provide a true color, and ability to deposit evenly in flesh and eggs. Zeaxanthin appears to be at least 1.5 times as potent as lutein. When administered to poultry in high doses, currently used carotenoid or carotenoid-containing compounds, such as canthaxanthin, alfalfa and cayenne pepper, cause abnormal red or purple colors in the flesh and color striations in yolks. High doses of lutein in feed has been shown to impart a greenish hue to poultry flesh and egg yolks. Beta-carotene does not deposit well in the flesh of poultry, and canthaxanthin apparently deposits in the iris of the eye. Zeaxanthin, in contrast, imparts a yellow-red color even at high doses and deposits well in poultry flesh, based on high zeaxanthin-containing corn feed studies. In addition, at least some fish and crustaceans, such as shrimp, goldfish, and carp, apparently can convert zeaxanthin into the red-colored pigment astaxanthin, suggesting that feeding of zeaxanthin to such fish and crustaceans will enhance desirable red coloration.

Zeaxanthin is produced along with other carotenoids in certain plants, such as corn, marigolds, and alfalfa. Although farmers have fed these plants to poultry, such diet supplementation is impractical due to the expense and lack of consistency in the amounts of zeaxanthin produced by such plants.

Prior attempts to purify zeaxanthin from natural sources have suffered from low yields. Moreover, the costs involved in chemically synthesizing zeaxanthin using existing techniques have proven to be prohibitive. In addition, due to concern over the health risks of compounds produced synthetically, there is a preference to produce food additives naturally, such as by microbial biosynthesis.

The Official Publication of the American Association of Feed Control Officials provides a list of microorganisms that the U.S. Food and Drug Administration (FDA) considers to be "generally recognized as safe" (GRAS) for use as food additives and for use in the production of food additives. Concerns regarding government approval for food additives make it desirable to produce zeaxanthin using GRAS microorganisms. However, the present inventors are not aware of any GRAS microorganism capable of producing sufficient amounts of zeaxanthin for use in a commercial process.

Among FDA-approved GRAS strains is *NeoSpongiococcum*, the only alga presently designated as GRAS for feeding to poultry to enhance yellow pigmentation (21 C.F.R. §73,275). Several investigators have attempted to use *Neospongiococcum* and other algal microorganisms to synthesize carotenoids, but none have succeeded in isolating a microorganism capable of producing commercial amounts of zeaxanthin. In fact, investigators have simply reported that algae produce low quantities of total xanthophylls, of which zeaxanthin is just a component. (Xanthophylls are oxygen-containing carotenoids such as astaxanthin, canthaxanthin, cryptoxanthin, lutein, rhodoxanthin, torulene, and violaxanthin, in addition to zeaxanthin.) For example, U.S. Pat. No. 3,108,402 by Kathrein, issued Oct. 29, 1963, discloses the use of a *Neospongiococcum* microorganism to produce up to 300 milligrams (mg) of total xanthophylls per liter of fermentation medium.

Similarly, U.S. Pat. No. 2,949,700 by Kathrein, issued Aug. 23, 1960, discloses the use of non-GRAS *Chlorella* and *Chlorococcum* algae to produce up to about 180 mg xanthophyll per liter of fermentation medium.

Investigators have described the production of zeaxanthin by several non-GRAS bacteria, fungi, and sponges, but none of these procedures have been commercialized. See, e.g., U.S. Pat. No. 2,974,044 by Farrow et al., issued Mar. 7, 1961; U.S. Pat. No. 3,841,967 by Dasek et al., issued Oct. 15, 1974; U.S. Pat. No. 3,891,504 by Schocher et al., issued Jun. 24, 1975; U.S. Pat. No. 3,951,742 by Shepherd et al., issued Apr. 20, 1976; U.S. Pat. No. 3,951,743 by Shepherd et al., issued Apr. 20, 1976; European Patent Publication No. 0393690 by Misawa et al., published Oct. 24, 1990; and PCT International Publication No. WO 91/03571 by Gierhart, published Mar. 21, 1991.

SUMMARY OF THE INVENTION

The present invention is directed toward a process for producing zeaxanthin which includes mutating algal microorganisms, selecting from those mutated microorganisms a microorganism capable of producing zeaxanthin, culturing the selected microorganism in an effective medium to produce zeaxanthin, and recovering zeaxanthin produced by the selected microorganism. The present invention also provides microorganisms capable of producing zeaxanthin, formulations containing zeaxanthin produced by the disclosed process, and use of such formulations to enhance pigmentation and to reduce damage caused by reactive oxygen species and phototoxic molecules.

In accordance with an embodiment of the present invention, a process for producing zeaxanthin has been developed which includes culturing in an effective medium an algal microorganism capable of producing at least about 0.35 mg zeaxanthin per gram dry cell weight and recovering zeaxanthin produced by the microorganism. Preferred microorganisms are those of the genus *Neospongiococcum*. In one embodiment, microorganisms capable of producing at least about 0.35 mg zeaxanthin per gram dry cell weight are cultured in a continuous fermentation. A preferred continuous fermentation is one conducted in an effective medium at a temperature from about 30° C. to about 38° C., at a pH from about pH 5.5 to about pH 6.5, at a dissolved oxygen concentration of at least about 10%, and at a carbon dioxide partial pressure of less than 0.04 atm.

In one embodiment of the present invention, zeaxanthin is recovered by separating microorganisms capable of producing zeaxanthin from the effective medium to form a zeaxanthin-containing biomass. Recovery can include a step of washing the zeaxanthin-containing biomass at least once to remove at least a portion of the chlorophyll contaminants, thereby reducing undesirable green color.

In another embodiment, zeaxanthin is extracted from microorganisms producing zeaxanthin using organic solvents. The purity of zeaxanthin recovered by this method has been demonstrated to be at least about 90%, and up to about 100%.

In one embodiment of the present invention, zeaxanthin is produced by microorganisms capable of producing at least about 0.35 mg zeaxanthin per gram dry cell weight, wherein zeaxanthin comprises at least about 5% of their total carotenoid production. Preferably microorganisms are capable of producing at least about 1.75 mg zeaxanthin per gram dry cell weight, or at least about 25% of their total carotenoids as zeaxanthin. In another embodiment, zeaxanthin is produced by microorganisms capable of producing at least about 2.8 mg zeaxanthin per gram dry cell weight, or at least about 40% of their total carotenoids as zeaxanthin.

In accordance with another embodiment of the present invention, algal microorganisms capable of producing zeaxanthin are produced by mutating parental algal microorganisms and selecting from the mutated microorganisms a microorganism capable of producing at least about 0.35 mg zeaxanthin per gram dry cell weight. Preferred parental microorganisms are those of the genus *Neospongiococcum*. Most preferred parental microorganisms are those having the identifying characteristics of *Neospongiococcum excentrium* ATCC No. 40335 and mutants thereof.

In one embodiment, algal microorganisms are mutated by exposing them to a mutagen such as N-methyl-N-nitro-N-nitrosoguanidine, ultraviolet radiation, x-rays, gamma rays, ethylmethane sulfonate, nitrous acid, or mixtures thereof. After mutation, microorganisms capable of producing zeaxanthin are selected by exposing mutated microorganisms to a metabolic inhibitor selected from the group comprising isoprenoid pathway inhibitors, carotenoid biosynthesis inhibitors, free radical generators, and mixtures thereof. In one embodiment, mutated microorganisms are exposed to an isoprenoid pathway inhibitor such as nystatin, antimycin A, citrinin, mevinolin, saponin, amphotericin B, phosphorylated farnesyl compounds, azasqualenes, allylamine derivatives, thiocarbamates, pyrimidines, imidazoles, triazoles, morpholines, or mixtures thereof. In another embodiment, mutated microorganisms are exposed to a carotenoid biosynthesis inhibitor such as norflurazon, metflurazon, phenylfuranones, diphenylamine, nicotinic acid, oxyfluorfen, fluorfen, $\beta$-ionone, or mixtures thereof. In yet another embodiment, mutated microorganisms are exposed to a free radical generator such as duroquinone, other quinones, peroxides, UV light, X-rays, gamma rays, ozone, or mixtures thereof. Microorganisms capable of producing zeaxanthin can also be isolated on the basis of color, wherein the color is indicative of zeaxanthin production.

The present invention leads to the production of algal, preferably *Neospongiococcum*, microorganisms capable of producing at least about 0.35 mg zeaxanthin per gram dry cell weight, preferably wherein zeaxanthin comprises at least about 5% of the microorganisms total carotenoid production. In one embodiment of the present invention, algal, preferably *Neospongiococcum*, microorganisms capable of producing at least about 1.75 mg zeaxanthin per gram dry cell weight are produced. Preferably these microorganisms produce at least about 25% of their total carotenoids as zeaxanthin, are produced. In another embodiment, algal, preferably *Neospongiococcum*, microorganisms capable of producing at least about 2.8 mg zeaxanthin per gram dry cell weight are produced. Preferably these microorganisms produce at least about 40% of their total carotenoids as zeaxanthin.

Particularly preferred are *Neospongiococcum* strains having the identifying characteristics of *Neospongiococcum excentricum* ATCC No. 74108 (referred to herein as HZ1236/274), and mutants thereof wherein the mutants are capable of producing at least about 0.35 mg zeaxanthin per gram dry cell weight; *Neospongiococcum* strains having the identifying characteristics of *Neospongiococcum excentricum* ATCC No. 74109 (referred to herein as HZ1236/437), and mutants thereof wherein the mutants are capable of producing at least about 0.35 mg zeaxanthin per gram dry cell weight; and *Neospongiococcum* strains having the identifying characteristics of *Neospongiococcum excentricum* ATCC No. 74107 (referred to herein as HZ1236/538), and mutants thereof wherein the mutants are capable of producing at least about 0.35 mg zeaxanthin per gram dry cell weight.

A preferred embodiment of the present invention is a process to produce zeaxanthin including (a) mutating microorganisms of the genus *Neospongiococcum*, (b) selecting from the mutated microorganisms a microorganism capable of producing at least about 0.35 mg zeaxanthin per gram dry cell weight, (c) culturing the selected microorganism in an effective medium to produce desired amounts of zeaxanthin, and (d) recovering zeaxanthin produced by the selected microorganism. More preferred embodiments include the production and use of selected microorganisms capable of producing at least about 1.75 mgzeaxanthin per gram dry cell weight. Additional preferred embodiments include selected microorganisms capable of producing at least about 2.8 mg zeaxanthin per gram dry cell weight.

In accordance with another embodiment of the present invention, an algal microorganism capable of producing at least about 0.35 mg zeaxanthin per gram dry cell weight, preferably of the genus *Neospongiococcum*, is used to produce zeaxanthin in a process including culturing the microorganism to produce zeaxanthin and recovering zeaxanthin produced thereby. In a preferred embodiment, a mutated algal microorganism selected by its ability to produce at least 0.35 mg zeaxanthin per gram dry cell weight is used to produce zeaxanthin. Preferably the microorganism is of the genus *Neospongiococcum*.

Another embodiment of the present invention is a zeaxanthin-containing formulation which comprises algal microorganisms, preferably of the genus *Neospongiococcum*, capable of producing at least about 0.35 mg zeaxanthin per gram dry cell weight, wherein zeaxanthin comprises at least about 5% of said microorganism's total carotenoid production. In a preferred embodiment, a zeaxanthin-containing formulation comprising a zeaxanthin-containing biomass and animal feed is administered to animal foodstuffs to enhance pigmentation. Preferred animal foodstuffs include poultry, fish and crustaceans.

Other embodiments of the present invention include the use of zeaxanthin produced by algal microorganisms, preferably of the genus *Neospongiococcum*, to enhance pigmentation or to reduce damage caused by reactive oxygen species and phototoxic molecules.

DETAILED DESCRIPTION OF THE INVENTION

The present invention provides novel algal microorganisms that produce zeaxanthin, a process for producing such microorganisms, and a process for producing commercially feasible amounts of zeaxanthin using such microorganisms. The present invention further provides formulations containing zeaxanthin produced by the disclosed process and the use of such formulations to enhance pigmentation and to reduce damage caused by reactive oxygen species and phototoxic molecules.

Production of microorganisms capable of producing zeaxanthin

The present invention provides algal microorganisms capable of producing zeaxanthin. As used herein, a "microorganism capable of producing zeaxanthin," also referred to as a "zeaxanthin-producing microorganism," is a microorganism capable of producing at least about 0.35 mg zeaxanthin per gram dry cell weight. Preferably, a zeaxanthin-producing microorganism is also capable of producing at least about 5% of its total carotenoids as zeaxanthin. As used herein, the term "total carotenoids" refers to all of the carotenoids produced by the microorganism including, but not limited to, other xanthophylls such as lutein.

In accordance with one embodiment of the present invention, zeaxanthin-producing microorganisms are produced by mutating parental algal microorganisms and selecting for microorganisms that are capable of producing zeaxanthin. As used herein, a "parental microorganism" refers to any microorganism that is to be mutated with the object of obtaining a microorganism that produces more zeaxanthin than does the parental microorganism. Parental microorganisms include, but are not limited to, naturally-occurring, variant, previously mutated, or previously selected microorganisms. Parental and zeaxanthin-producing microorganisms of the present invention can be either recombinant or non-recombinant microorganisms.

In one embodiment of the present invention, parental algal microorganisms are exposed to a selective medium in which zeaxanthin-producing microorganisms are able to grow. In this manner, naturally-occurring mutants of the parental strain that are capable of producing zeaxanthin can be isolated. In a preferred embodiment of the present invention, parental microorganisms are subjected to at least one round of chemical or physical mutagenesis in order to increase the rate of mutagenesis, thereby increasing the probability of obtaining a zeaxanthin-producing microorganism. As used herein, a "mutated microorganism" is a mutated parental microorganism in which a mutation(s) either occurs naturally or is the result of exposure to a mutagen.

In the present invention, preferred parental microorganisms are algae. Especially preferred are algae of the genus *Neospongiococcum*. The most preferred parental microorganism is *Neospongiococcum excentricum* ATCC No. 40335, the subject of co-pending U.S. Pat. application Ser. No. 07/474,248 by Liao et al, filed Feb. 5, 1990.

*Neospongiococcum* algae have advantages over other types of algae, including the capability to grow to cell densities at least four-fold higher than those achieved by other xanthophyll-producing algae, such as, for instance, *Chlorella* (U.S. Pat. No. 3,280,502 by Farrow et al., issued Oct. 25, 1966), or by certain *Flavobacterium multivorum* strains (PCT International Publication No. WO 91/03571 to Gierhart, published Mar. 21, 1991). Higher cell densities lead to more product per unit volume, thereby lowering production costs. Also, intracellular products in *Neospongiococcum* are bioavailable to animals since animals can digest *Neospongiococcum* cell walls and obtain the intracellular products. Thus, whole *Neospongiococcum* cells can be fed directly to animals. In contrast, most xanthophyll-producing algae, such as *Chlorella*, cannot be used directly as animal feed because the cell walls of these algae are composed of cellulose-based materials that cannot be digested by most non-ruminants. The ability to feed whole cells to animals, such as poultry, obviates the need for additional downstream recovery processing steps, thereby lowering production costs and reducing zeaxanthin losses. Moreover, because of the higher zeaxanthin production capabilities obtained in accordance with the present invention, less total weight of cells must be used to obtain equivalent amounts of zeaxanthin.

In one embodiment of the present invention, algal microorganisms, preferably those of the genus *Neospongiococcum*, are exposed to a chemical or physical mutagen to obtain microorganisms that produce zeaxanthin. Preferred mutagens include, but are not limited to, N-methyl-N-nitro-N-nitrosoguanidine (NTG), ultraviolet radiation, x-rays, gamma rays, ethylmethane sulfonate, and nitrous acid. The mutagens can be used either singly or in mixtures. The most preferred mutagen for use in the present invention is NTG. In one embodiment of the present invention, *Neospongiococcum excentricum* ATCC No. 40335 microorganisms are exposed to a buffer solution containing NTG. After exposure, the microorganisms are rinsed, resuspended in a growth medium, such as a yeast extract/peptone/glucose (YEP) medium, and incubated overnight at about 35° C. to obtain mutated *Neospongiococcum* microorganisms. Mutated microorganisms can then be grown on solidified growth medium for between about 5 and about 7 days at about 35° C. to obtain single colonies. As used herein, solidified growth medium refers to a growth medium to which a solidifying agent such as gelatin, agarose, or agar has been added. A preferred solidified growth medium of the present invention is a yeast extract/peptone/glucose medium to which agar has been added (YEP-agar). Preferably, microorganisms are exposed to about 25 micrograms (μg) NTG per ml citrate buffer for about 30 minutes at a temperature of about 35° C.

Another aspect of the present invention is the selection of desired mutated algal microorganisms. Preferred selection strategies to identify mutated microorganisms that produce zeaxanthin include selection by color and selection by resistance to (i.e., ability to grow in the presence of) metabolic inhibitors including, but not limited to, isoprenoid pathway inhibitors, carotenoid biosynthesis inhibitors, and free radical generators. Metabolic inhibitors can be used either singly or in mixtures. Selected microorganisms (i.e., those microorganisms that are selected according to the selection strategies of the present invention) are grown in an effective medium to determine the amount of zeaxanthin the microorganisms are capable of producing. Zeaxanthin production by selected strains can be measured in a variety of ways including, but not limited to, functional and chromatographic assays. In the present invention, the preferred method to measure microbial zeaxanthin production is by reverse phase high pressure liquid chromatography (HPLC).

In accordance with one embodiment of the present invention, mutated microorganisms are grown on a solidified growth medium, such as YEP-agar, and selected on the basis of color. Selection of mutated microorganisms by their colored appearance is a useful method to identify microorganisms producing zeaxanthin. Microorganisms capable of producing zeaxanthin usually appear olive green, yellow, reddish-yellow, orange, or red in color. As used herein, these colors are referred to as colors indicative of zeaxanthin production. Often zeaxanthin-producing algal microorganisms also exhibit a background green hue due to chlorophyll production. In the present invention, microorganisms selected on the basis of color are referred to as color-selected microorganisms. Preferred colors for color-selected microorganisms include yellow, reddish-yellow, orange, and red. In a preferred embodiment, mutated microorganisms are grown on solid growth medium, such as YEP-agar, for between about 5 and about 7 days at about 35° C. to select for zeaxanthin producers as indicated by colored appearance.

In accordance with another embodiment of the present invention, mutated microorganisms are selected as zeaxanthin producers by their ability to grow in the presence of a metabolic inhibitor. Metabolic inhibitors are preferably selected from the group comprising isoprenoid pathway inhibitors, carotenoid biosynthesis inhibitors, and free radical generators. The inhibitors can be used either singly or in mixtures. Microorganisms capable of zeaxanthin production can also be selected by a combination of color selection and ability to grow in the presence of a metabolic inhibitor.

In one embodiment, mutated microorganisms are selected as zeaxanthin producers by their ability to grow in a medium containing isoprenoid pathway inhibitors. Isoprenoid pathway inhibitors are compounds that inhibit one or more steps in the isoprenoid synthetic pathway, including steps in the sterol synthetic pathway. Such inhibitors include, but are not limited to, nystatin, antimycin A, citrinin, mevinolin, saponin, amphotericin B, phosphorylated farnesyl compounds, azasqualenes, allylamine derivatives, thiocarbamates, pyrimidines, imidazoles, triazoles, morpholines, and mixtures thereof. The preferred isoprenoid inhibitor for use in the present invention is nystatin, which apparently disrupts cellular membranes by binding to membrane-bound ergosterol. In one embodiment, mutated microorganisms are selected for zeaxanthin production on a solid growth medium, such as YEP-agar, containing at least about 1 μg nystatin per ml growth medium, preferably between about 1 μg and about 20 μg nystatin per ml. In a preferred embodiment, mutated microorganisms are grown on a medium containing between about 5 μg/ml and about 7 μg/ml nystatin for about 10 days at about 35° C.

In another embodiment of the present invention, mutated microorganisms are selected as zeaxanthin producers by their ability to grow in a medium containing a compound that inhibits the carotenoid biosynthetic pathway. Inhibitors of the carotenoid biosynthetic pathway are compounds that inhibit one or more steps in the pathway by which carotenoids are synthesized. Carotenoid biosynthesis inhibitors include, but are not limited to, norflurazon, metflurazon, phenylfuranones, diphenylamine, nicotinic acid, oxyfluorfen, fluorfen, β-ionone, and mixtures thereof. The preferred carotenoid biosynthesis inhibitor for use in the present invention is norflurazon, which blocks desaturation reactions required to produce carotenoids. In one embodiment, mutated microorganisms are selected for zeaxanthin production on a solid growth medium, such as YEP-agar, containing between about 10 nanograms (ng) and about 100 ng norflurazon per ml for about 10 days at about 35° C. A preferred concentration of norflurazon in the medium is between about 60 ng/ml and about 100 ng/ml.

In another embodiment of the present invention, mutated microorganisms are selected as zeaxanthin producers by their ability to grow in a medium containing a compound that generates free radicals (i.e., a free radical generator). It is believed that carotenoids, due to their antioxidant properties, are able to protect cells from damage caused by free radicals. However, the present inventors are unaware of the use of free radical generating compounds to select for microorganisms capable of producing large amounts of carotenoids such as zeaxanthin. Free radical generators include, but are not limited to quinones, peroxides, UV light, X-rays, gamma rays, ozone, and mixtures thereof. Preferred free radical generators, such as quinones and peroxides, are those that are easily absorbed by the microorganisms and are not mutagenic. A most preferred free radical generator for use in the present invention is duroquinone. In one embodiment, mutated microorganisms are selected for zeaxanthin production by growing the microorganisms on solid growth medium, such as YEP-agar, containing between about 20 micromolar (μM) and about 100 μM duroquinone for about 10 days at about 35° C. A preferred concentration of duroquinone is about 55 μM.

In one embodiment of the present invention, parental algal microorganisms are exposed to a suitable mutagen, preferably NTG to obtain mutated microorganisms. Microorganisms capable of producing zeaxanthin are selected from the mutated microorganisms on the basis of color and ability to grow in the presence of isoprenoid pathway inhibitors, carotenoid biosynthesis inhibitors, and/or free radical generators. Selected microorganisms capable of producing at least about 0.35 mg zeaxanthin per gram dry cell weight are isolated and cultured in an effective medium. The above mutation-selection process can be repeated more than once to obtain microorganisms capable of producing even higher levels of zeaxanthin. Preferred selected strains should be capable of producing at least about 0.70 mg zeaxanthin per gram dry cell weight, more preferably at least about 1.75 mg zeaxanthin per gram dry cell weight, and most preferably at least about 2.8 mg zeaxanthin per gram dry cell weight. Additionally, selected microorganisms should be capable of producing at least about 5% of their total carotenoids as zeaxanthin, preferably at least about 10%, more preferably at least about 25%, and most preferably at least about 40% of their total carotenoids as zeaxanthin.

Preferred microorganisms of the present invention comprise microorganisms of the genus *Neospongiococcum* and mutants thereof, wherein "mutants thereof" are capable of producing at least about 0.35 mg zeaxanthin per gram dry cell weight.

One preferred algal microorganism of the present invention is *Neospongiococcum excentricum* ATCC No. 74108 (HZ1236/274) which has an identifying characteristic of being able to produce about 3.5 mg zeaxanthin per gram dry cell weight. An additional identifying characteristic is that about 40% to 50% of the total carotenoids produced by ATCC No. 74018 (HZ1236/274) have been demonstrated to comprise zeaxanthin. *Neospongiococcum excentricum* HZ1236/274 was deposited with the American Type Culture Collection (ATCC), 12301 Parklawn Drive, Rockville, Md., 20852-1776, on Sep. 27, 1991, under number ATCC 74018.

Another preferred algal microorganism of the present invention is *Neospongiococcum excentricum* ATCC No. 74109 (HZ1236/437) which has an identifying characteristic of being able to produce about 3 mg zeaxanthin per gram dry cell weight. An additional identifying characteristic is that about 40% of the total carotenoids produced by ATCC No. 74109 (HZ1236/437) have been demonstrated to comprise zeaxanthin. *Neospongiococcum excentricum* HZ1236/437 was also deposited with the ATCC on Sep. 27, 1991 under number ATCC 7409.

Yet another preferred algal microorganism of the present invention is *Neospongiococcum excentricum* ATCC No. 74107 (HZ1236/538) which has an identifying characteristic of being able to produce about 3 mg zeaxanthin per gram dry cell weight. An additional identifying characteristic is that about 40% of the total carotenoids produced by ATCC No. 74107 (HZ1236/538) have been demonstrated to comprise zeaxanthin. *Neospongiococcum excentricum* HZ1236/538 was also deposited with the ATCC on Sep. 27, 1991 under number ATCC 74107.

ATCC No. 74108 (HZ1236/274), ATCC No. 74109 (HZ1236/437), and ATCC No. 74107 (HZ1236/538) were deposited under the Budapest Treaty on the International Recognition of the Deposit of Microorganisms for the purpose of Patent Procedure. All restrictions on the availability to the public of the materials so deposited will be irrevocably removed upon the granting of a patent. Each deposit will be stored for a period of at least five years after the most recent request for the furnishing of a sample of the deposited microorganism is received by the ATCC, and, in any case, for a period of at least 30 years after the date of the deposit.

It will be obvious to one skilled in the art that the present invention includes zeaxanthin-producing microorganisms that can be obtained by genetically-engineering organisms to produce zeaxanthin. For example, it is within the purview of the present invention to transform microorganisms with genes encoding enzymes of the zeaxanthin biosynthetic pathway obtained from algal zeaxanthin-producing microorganisms, such as those of the genus *Neospongiococcum*. Such genes can be natural DNA sequences or sequences obtained by mutagenesis and selection techniques as described herein and elsewhere. Conversely, algal microorganisms, such as *Neospongiococcum*, can be transformed with zeaxanthin biosynthetic pathway genes isolated from algal or other suitable organisms.

Zeaxanthin Production

The present invention provides a process to produce zeaxanthin by culturing algal microorganisms capable of producing zeaxanthin in an effective medium and recovering zeaxanthin therefrom.

In accordance with the present invention, algal microorganisms capable of producing zeaxanthin, are cultured in an effective medium, herein defined as any medium capable of promoting zeaxanthin production. Preferably, the effective medium also promotes algal growth. The algal zeaxanthin-producing microorganisms of the present invention can be cultured in conventional fermentation modes, which include, but are not limited to, batch, fed-batch, and continuous.

In one embodiment of the present invention, algal microorganisms, preferably of the genus *Neospongiococcum*, are cultured in a continuous fermentation process in which fresh fermentation medium is added and spent fermentation broth is removed either without interruption or on a periodic basis. During the fermentation, variables including the temperature, oxygen. content, carbon dioxide content, pH, and rate of carbon source addition are kept under control in such a way as to maximize the production of zeaxanthin without unduly limiting the length of time during which successful fermentation can be accomplished. Suitable fermentation conditions and procedures are similar to those described in co-pending U.S. Patent Application Ser. No. 07/524,140 by Bailey et al, filed May 15, 1990. Bailey et al describe a high productivity, continuous fermentation process for carotenoid-producing microorganisms, including *Neospongiococcum excentricum* ATCC No. 40335.

The present invention involves culturing algal microorganisms capable of producing zeaxanthin while diluting the fermentation broth, or effective medium, by the addition of fresh fermentation medium. The fresh fermentation medium is generally an aqueous solution which includes a carbon source provided in an amount that limits the growth rate of the microorganisms. In particular, the fresh fermentation medium can be water, or water with nutrients, such as glucose, and other materials added to it.

The fermentation broth can be diluted either by increasing the overall volume of the broth by adding fresh fermentation medium or, preferably, by maintaining a substantially constant volume of fermentation broth by adding fresh fermentation medium and removing spent fermentation broth. In the latter case, the dilution rate (D) is equal to the volumetric flow rate of fresh fermentation medium into the fermentation vessel and spent fermentation broth out of the vessel, divided by the volume of the fermentation broth. The units for D are reciprocal time, and for present purposes will be $hr^{-1}$ unless indicated otherwise. Dilution is equal to the number of vessel liquid volumes which pass through the vessel per hour, and is the reciprocal of mean residence time.

The addition of fresh fermentation medium and the removal of spent fermentation broth can be either constant or periodic, but is preferably constant. The addition of fresh fermentation medium and the removal of spent fermentation broth can either be simultaneous or not, but is preferably simultaneous.

In the case of maintaining a relatively constant volume of fermentation broth for the growth of a typical culture, dilution is typically effective at between about 0.03 $hr^{-1}$ to about 0.13 $hr^{-1}$.

As used herein, the term "growth rate", indicated by the symbol "u", is the mass of cells formed per mass of cells in the fermentation broth per unit time. Unless otherwise indicated, the units for growth rate are $hr^{-1}$. At steady state, the dilution rate is equal to the growth rate (D=u) in the continuous fermentation method of the present invention. Dilution rate (D) is dictated by the maximum growth rate ($u_{max}$) of a particular microorganism. One can set the dilution rate in continuous culture at any level less than $u_{max}$. For optimal productivity, D is preferably from about 25% to about 95% of $u_{max}$, and more preferably is about 90% of $u_{max}$. The system will tend to be more unstable as $u_{max}$ is approached. Washout occurs if D is greater than u.

It should be recognized that with the introduction of fresh fermentation medium, the nutrient levels in the fermentation broth must be maintained at concentrations sufficient to support growth and/or production of zeaxanthin. Such nutrients can be added either in the fresh fermentation medium or independently of it. Specifically, such nutrients include sources of carbon: nitrogen; phosphates; sulfates; and magnesium, iron, and other trace metals.

Sources of assimilable carbon include but are not limited to sugars and their polymers, including starches, dextrin, saccharose, maltose, lactose, glucose, mannose, sorbose, arabinose, xylose, levulose, cellobiose, and molasses; fatty acids; and polyalcohols such as glycerine. Preferred carbon sources in the present invention include monosaccharides, disaccharides, and trisaccharides. The most preferred carbon source is glucose.

Sources of assimilable nitrogen include, but are not limited to, inorganic nitrogen compounds such as ammonium salts and substances of animal, vegetable and/or microbial origin such as protein hydrolysates, microbial biomass hydrolysates, soy meal, fish meal, meat meal, meat extract, peptone, tryptone, corn steep liquor, yeast extract, and amino acids. Preferred nitrogen sources include yeast extract, peptone, and ammonium sulfate.

The effective medium can contain other compounds such as vitamins, growth promoters, or pigment formation promoters. Such compounds can be present in carbon, nitrogen, or mineral sources in the effective medium or can be added specifically to the medium.

An embodiment of the present invention includes conducting a fermentation while restricting the carbon source in the fermentation to a growth rate-limiting level. In this manner, the time of fermentation can be extended indefinitely and the yield of product can be increased. This aspect of the present invention involves restricting the rate of addition of the carbon source to a rate-limiting level. Preferably, all other nutrients necessary for growth are present in excess compared with the carbon source. Without intending to be bound by theory, it is believed that by restricting the availability of the carbon source, the production of toxins is substantially reduced because microorganisms will be forced to preferentially utilize available carbon for growth.

The rate of addition of the carbon source can be monitored and the carbon source can be fed at a rate to achieve the desired restricted growth rate in the range of between about 25% of $u_{max}$ and about 95% $u_{max}$, more preferably about 90% of $u_{max}$.

In a preferred embodiment of the present invention, the fermentation broth, or effective medium, is diluted with fresh fermentation medium and the carbon source feed rate is restricted to a rate-limiting level. Preferably, this method includes three phases: (1) an inoculation phase; (2) a fed-batch growth phase; and (3) a carbon source-limited, continuous culture growth phase. The inoculation phase includes providing an inoculum of actively growing microorganisms to a fermentation vessel. The fed-batch growth phase includes propagating microorganisms in the fermentation vessel with continuous medium additions while maintaining the carbon source concentration at less than 5 grams per liter. Typically, the carbon source is between about 1 g/l and about 5 g/l during the fed-batch period. During the transition from the fed-batch phase to the steady state continuous phase, the rate of continuous feed of fresh fermentation medium containing the carbon source is gradually increased. The continuous fermentation phase commences when a desired steady state cell concentration is attained.

Preferably, the carbon source is a carbohydrate, such as glucose. Prior to switching to the glucose-limited, continuous culture growth phase, glucose is depleted to a minimal concentration. This concentration is as low as is practical, typically about 1 g/l. The fermentation is then switched to the glucose-limited, continuous culture growth phase. A continuous feed stream, including glucose and otherwise nutritionally balanced for growth (i.e., including nutrients such as nitrogen, potassium, phosphate, iron, sulfate, citric acid, magnesium, and other trace metals) is introduced to the fermentation medium at an initially low dilution rate. The dilution rate is then gradually increased until the growth rate of the microorganisms is almost as great as the maximum growth rate achieved during the batch growth phase and a desired steady-state dilution rate is attained. Preferably D is about 90% $u_{max}$. Fresh fermentation medium is added at a rate equal to the removal rate for the spent fermentation broth.

Control of temperature, pH, oxygen, and carbon dioxide are other important parameters in culturing zeaxanthin-producing microorganisms to obtain high growth rates and, more particularly, high yields of zeaxanthin. In the preferred process, culturing, or fermentation, is conducted at a temperature from about 30° C. to about 38° C., at a pH from about pH 5.5 to about pH 6.5, at a dissolved oxygen content of at least about 10%, and at a carbon dioxide partial pressure of less than about 0.04 atm. Under the most preferred conditions, the culturing is conducted at about 36° C., at a pH of about pH 6.0, at a dissolved oxygen content of greater than about 10%, and at a carbon dioxide partial pressure of less than about 0.04 atm.

After zeaxanthin has been produced by the algal microorganisms in the desired amounts, zeaxanthin can be recovered by recovering the zeaxanthin-producing microorganisms as a zeaxanthin-containing biomass. As used herein, the term zeaxanthin-containing biomass refers to zeaxanthin-containing microorganisms recovered from a fermentation medium following the intracellular production of zeaxanthin by such microorganisms.

In one embodiment of the present invention algal zeaxanthin-containing biomass is recovered for use as a feed additive to enhance the pigmentation of animal foodstuffs. As used herein, enhancement of pigmentation describes a process by which administration of zeaxanthin imparts a yellow or reddish-yellow color to the flesh, skin, other body parts, and/or yolks of animal foodstuffs to which zeaxanthin is administered, or imparts a similar coloration to a composition, such as a food product (foodstuffs other than animal foodstuffs) or a cosmetic, to which zeaxanthin is added. If the animal foodstuff converts zeaxanthin to astaxanthin, the animal may display a red coloration. Animal foodstuffs are animals which are raised as food. Such animals include, but are not limited to, poultry, fish, and crustaceans.

A preferred source of zeaxanthin-containing biomass according to the present invention is *Neospongiococcum* due to the bioavailability of zeaxanthin in *Neospongiococcum* zeaxanthin-producing microorganisms. Zeaxanthin-containing *Neospongiococcum* biomass can be used directly as a feed additive to enhance the pigmentation of animal foodstuffs.

Zeaxanthin-containing *Neospongiococcum* biomass for use as a feed additive can be recovered simply by separating the zeaxanthin-containing microorganisms from the fermentation medium. Preferred separation techniques include, but are not limited to, centrifugation and filtration. In a preferred embodiment, zeaxanthin-containing *Neospongiococcum* biomass is recovered by separating zeaxanthin-containing microorganisms by centrifugation, washing the biomass at least once with an aqueous solution to reduce undesirable green color by removing at least a portion of chlorophyll contaminants, and spray drying the biomass to obtain a biomass powder. Preferably, the biomass is dried to obtain a powder having a moisture content of about 3% to about 5%.

Recovery of zeaxanthin-containing biomass from algal zeaxanthin-producing microorganisms that have non-digestible cell walls requires an additional step of cell lysis prior to spray drying of the biomass. Such analysis can be accomplished by using physical, chemical, or enzymatic methods known to one of skill in the art.

In one embodiment of the present invention, the total carotenoid content of zeaxanthin-containing biomass powder is typically at least about 5 mg, and preferably at least about 7 mg, per gram biomass. In accordance with the present invention, at least about 5% of the total carotenoid content is zeaxanthin, preferably, at least about 10%, more preferably at least about 25%, and most preferably at least about 40%.

Alternatively, zeaxanthin can be purified free from algal microorganisms capable of producing zeaxanthin using standard techniques. Standard methods to purify zeaxanthin from microbial sources include the use of organic solvents, both to extract zeaxanthin from zeaxanthin-producing microorganisms, and to purify zeaxanthin from other contaminants. In a preferred embodiment of the present invention, standard purification techniques may be used to recover zeaxanthin from zeaxanthin-producing microorganisms to obtain substantially pure zeaxanthin having a purity of above about 90%, preferably at least about 97%, and most preferably close to 100%.

Substantially pure zeaxanthin can be formulated into a zeaxanthin-containing formulation and used to enhance the pigmentation of foods and cosmetics as well as to reduce damage caused by reactive oxygen species and phototoxic molecules. As used herein, reactive oxygen species are molecules that oxidize other molecules, often leading to, or resulting in, cell or tissue damage. Reactive oxygen species include photosensitizers, singlet oxygen, and oxygen free radicals. As used herein, phototoxic molecules refer to agents, such as light, which can degrade or otherwise inactivate light-sensitive compounds, and which can cause tissue damage (including cell and organ damage) in plants and animals. An effective amount of zeaxanthin is an amount which effectively reduces damage caused by reactive oxygen species and phototoxic molecules. For example, zeaxanthin can be used in mammals to prevent or treat certain forms of cancer and to reduce both external and internal cellular, tissue or organ damage caused by reactive oxygen species.

Zeaxanthin-containing formulations can be administered either internally (including, but not limited to, oral, nasal, intravenous, intradermal, and intraperitoneal modes of administration) or externally (including, but not limited to, topical administration). For example, zeaxanthin-containing formulations can be added to sunscreens and other oils and lotions to reduce damage to the skin caused by reactive oxygen species.

Zeaxanthin-containing formulations can also be added in an effective amount to light-sensitive and/or oxygen-sensitive compounds in order to stabilize and reduce damage caused to such compounds in the presence of light or oxygen.

Pigment Enhancement

The present invention provides pigment enhancement zeaxanthin-containing formulations and a method to administer the formulations to animals to enhance pigmentation. An effective amount of zeaxanthin to enhance pigmentation is an amount that provides a desirable yellow to reddish-yellow color to the flesh, skin, other body parts, and/or egg yolk of an animal. If the animal is able to convert zeaxanthin to astaxanthin, the animal may display a red coloration. According to the present invention, algal microorganisms are cultured to produce zeaxanthin and zeaxanthin-containing biomass powder is recovered as described above. The recovered zeaxanthin-containing powder can be formulated into a zeaxanthin-containing formulation for administration to an animal foodstuff. A preferred zeaxanthin-containing formulation comprises zeaxanthin-containing biomass powder combined with animal feed.

In one embodiment of the present invention, *Neospongiococcum* microorganisms capable of producing zeaxanthin are cultured and zeaxanthin-containing biomass powder is recovered by separating zeaxanthin-containing microorganisms from the fermentation medium to obtain a zeaxanthin-containing biomass, washing the resultant biomass, and spray drying the biomass. The recovered zeaxanthin-containing biomass powder can be administered directly to animals including, but not limited to, poultry, fish, and crustaceans to enhance pigmentation of the flesh, skin, other body parts, and/or egg yolks of such animals.

In a preferred embodiment, *Neospongiococcum* zeaxanthin-containing biomass powder is blended with poultry feed. The amount of powder added to the poultry feed is based on the powder's total xanthophyll content. Preferred zeaxanthin-containing formulations comprise between about 10 and about 40 grams of xanthophylls per ton of feed. Most preferred formulations contain about 40 grams of xanthophylls per ton of feed.

The following experimental results are provided for purposes of illustration and are not intended to limit the scope of the invention. It is specifically noted that the parameters, such as concentrations, times, temperatures, and other reaction conditions, as set forth in the following examples, are embodiments of the present invention and are not to be understood as limitations. Suitable ranges of such parameters will be within the skill of an ordinary artisan.

EXAMPLE 1

Isolation of Zeaxanthin Producer N. excentricum HZ1236

*Neospongiococcum excentricum* ATCC No. 40335 was grown in a shake flask fermentation at 35° C. to an optical density (O.D.) at.! 620 nm of between about 1.0 and 2.0 in yeast-extract/peptone (YEP) media (3.0 g/l yeast extract, 5.0 g/l peptone, and 20 g/l glucose). Cells from 10 ml of the culture were harvested by centrifugation and washed twice with sterile citrate buffer (0.1M sodium citrate, pH 5.5). The cells were resuspended in 10 ml citrate buffer. 250 $\mu$l of 1 $\mu$g/$\mu$l NTG was added to the suspended cells to give a final NTG concentration of 25 $\mu$g/ml. (These conditions typically kill 65% to 80% of the cells.) The cells were mutagenized by gently rocking them at 35° C. for 30 minutes in the dark. After mutagenesis, the cell suspension was centrifuged and the cell pellet was washed twice with citrate buffer. The mutagenized cells were resuspended in 10 ml YEP and incubated at 35° C. overnight. After overnight growth, the cell culture was diluted with citrate buffer to a concentration at which approximately 50 colonies would grow on a 100 mm plate. Aliquots of the diluted culture were spread onto plates containing solidified YEP media (YEP media containing 20 g/l agar) and allowed to grow for 5 to 7 days at 35° C. After growth, colonies were visually scored on the basis of color and transferred onto fresh solidified YEP plates containing 5 $\mu$g/ml nystatin and grown for an additional 10 days to select for zeaxanthin producers. An olive green algal microorganism, referred to as *Neospongiococcum excentricum* HZ1236, was found to grow on a solidified YEP plate containing 5 $\mu$g/ml nystatin and was isolated. When grown in a shake flask in YEP medium, *S. excentricum* HZ1236 was found to typically produce about 10–15% of its total carotenoid production as zeaxanthin. This strain was found to typically produce zeaxanthin and lutein at a zeaxanthin-to-lutein (Z:L) ratio of about 0.15. In contrast, the parent strain *N. excentricum* ATCC No. 40335 typically produces 2–4% of its total carotenoids as zeaxanthin at a Z:L ratio of 0.03 to 0.06.

EXAMPLE 2

Isolation of Zeaxanthin Producer *N. excentricum* HZ1236/274

*N. excentricum* HZ1236 was re-exposed to NTG using the conditions described in Example 1. Mutagenized colonies were grown as described in Example 1, except that colonies which grew on solidified YEP plates were transferred to fresh solidified YEP plates containing 7 $\mu$g/ml nystatin for an additional 10 days to select for microorganisms that produced higher amounts of zeaxanthin. *Neospongiococcum excentricum* ATCC No. 74108 (also called HZ1236/274), a yellow-green colony, was found to grow on a solidified YEP plate containing 7 $\mu$g/ml nystatin and was isolated. When grown in a 2-liter fermentor under the conditions described in Example 4, *N. excentricum* ATCC No. 74018 (also called HZ1236/274) was found to typically produce about 3.5 mg zeaxanthin per gram dry cell weight. Typically, about 50% of the strain's total carotenoids were found to be zeaxanthin. *N. excentricum* ATCC No. 74108 (also called HZ1236/274) was also found to typically produce zeaxanthin and lutein at a Z:L ratio of about 1.1.

EXAMPLE 3

Isolation of Zeaxanthin Producer *N. excentricum* HZ1236/538

*N. excentricum* HZ1236 was re-exposed to NTG using the conditions described in Example 1. Mutagenized colonies were grown as described in Example 1, except that colonies which grew on solidified YEP plates were transferred to fresh solidified YEP plates containing 55 $\mu$M duroquinone for an additional 10 days to select for microorganisms that produced higher amounts of zeaxanthin. *Neospongiococcum excentricum* ATCC No. 74107 (also called HZ1236/538), a orange-green colony, was found to grow on a solidified YEP plate containing 55 $\mu$M duroquinone and was isolated. When grown in a 2-liter fermentor under the conditions described in Example 4, *N. excentricum* ATCC No. 74107 (also called HZ1236/538) was found to typically produce about 3 mg zeaxanthin per gram dry cell weight. About 40% of the strain's total carotenoids were found to be zeaxanthin. *N. excentricum* ATCC No. 74107 (also called HZ1236/538) was found to typically produce zeaxanthin and lutein at a Z:L ratio of about 0.60.

EXAMPLE 4

Preparation of Inoculum and Medium

An inoculum was prepared using a strain of *Neospongiococcum excentricum* ATCC No. 74108 (also called HZ1236/274). Initially, a Yeast-extract/Peptone (2X YEP) inoculum medium was prepared comprising 6.0 g/l of Difco yeast extract, and 10.0 g/l of Bacto-peptone in 960 ml deionized water. The mixture was sterilized by autoclaving at 121° C. for 25 minutes. Subsequent to autoclaving, 40 ml of a 50% glucose solution was added. A single colony of *N. excentricum* was inoculated into a 1-liter shaker flask containing 200 ml of the above-described inoculum medium. The flask was incubated in a gyrotory shaker at 400 rpm and at 35° C.$\pm$120 C. The flask was incubated until an optical density of 7 to 10 (absorbance at 620 nm) was attained.

A fermentation medium was prepared which includes 3.88 g/l of $KH_2PO_4$, 1.50 g/l of Amberex yeast extract, 2.75 g/l of $(NH_4)_2SO_4$, and 0.20 g/l of citric acid in 9 l of deionized water. This solution was autoclaved for 60 minutes at 121° C. Subsequently, the autoclaved solution was brought to 5 g/l of glucose, 5.0 ml/l of trace metal 8 solution, 4.5 ml/l of $MgSO_4 \cdot 7H_2O$, and 0.1 g/l of $FeSO_4 \cdot 7H_2O$.

Trace metal 8 solution includes, in 6.0 liters of deionized water, 200 ml of concentrated hydrochloric acid (97%), 114 grams of CaCl·2H$_2$O, 12.3 grams of manganese sulfate, 0.314 grams of copper sulfate·5H$_2$O, 1.6 grams of cobalt chloride·6H$_2$O, 9.12 grams of boric acid, 17.65 grams of zinc sulfate·7H$_2$O, 0.48 grams of sodium molybdenate·2H$_2$O, 0.8 grams of vanadyl sulfate·2H$_2$O, 0.4 grams of nickel nitrate·6H$_2$O, 0.4 grams of sodium selenite, and 2.5 grams of sodium citrate. After all solids were added and fully dissolved, the final volume was brought to 10 liters with deionized water.

The pH of the fermentation medium was approximately pH 4.8. Ammonium hydroxide solution (14%) was used to adjust the pH to pH 6.0 prior to inoculation. Pre-inoculation conditions were as follows: temperature=36° C.±1° C.; pH=6.0±0.2; agitation=400 rpm; aeration=1 vvm; and dissolved oxygen=100% saturation.

The inoculum was aseptically transferred to the fermentation vessel. The final concentration of inoculum in the vessel was 5% by volume. The initial optical density was about 0.5.

For the fed-batch phase, the fresh fermentation medium feed includes 500 g/l of glucose, which was autoclaved for 40 minutes at 121° C., with the subsequent addition of 28.57 ml/l of MgSO$_4$·7H$_2$O and 5.72 ml/l of H$_3$PO$_4$.

The continuous phase fresh fermentation medium feed stream includes sterilized glucose and 0.048 grams of KH$_2$PO$_4$ per gram of glucose, 0.0025 grams of FeSO$_4$·7H$_2$O per gram of glucose, 0.003 grams of anhydrous citric acid per gram of glucose, 0.11 ml of one molar MgSO$_4$·7H$_2$O per gram of glucose, and 0.125 ml of trace metal 8 solution per gram of glucose.

EXAMPLE 5

Production of Zeaxanthin Using *N. excentricum* HZ1236/274

The following example illustrates the use of the process parameters described above to produce zeaxanthin in a pilot plant fermentation.

A. Preparation of inoculum: A 14 liter fermentor was charged with 7 liters water containing 31 g KH$_2$PO$_4$, 30 g Amberex 695 yeast extract, 22 g (NH$_4$)$_2$SO$_4$, and 1.0 ml of MAZU 204 antifoam. The entire contents of the vessel were steam sterilized at 121° C. for 90 min. A 500-ml solution of the remaining nutrients were then aseptically filter-sterilized into the fermentor. This nutrient solution contained 160 g glucose, 40 ml of trace metal 8 solution, 9 g MgSO$_4$·7H$_2$O, 0.8 g FeSO$_4$·7H$_2$O, and 1.6 g citric acid. This fermentor was then inoculated with 500 ml of a 48-hr *Neospongiococcum excentricum* ATCC No. 74108 (also called HZ1236/274) culture grown in YEP (9 g/l yeast extract, 15 g/l peptone, and 10 g/l glucose). Aeration was kept at 1.0–1.2 vvm with the agitation at 400–600 rpm throughout the run. The pH was controlled at 6.0 with anhydrous ammonia addition.

When the residual glucose decreased to approximately 5 g/l, a nutrient feed was initiated consisting of the following components:

| | |
|---|---|
| Glucose | 320 g/l |
| KH$_2$PO$_4$ | 62 g/l |
| (NH$_4$)SO$_4$ | 44 g/l |
| Trace metal 8 | 80 ml/l |
| MgSO$_4$·7H$_2$O | 17.8 g/l |
| FeSO$_4$·7H$_2$O | 1.6 g/l |
| Citric acid | 3.2 g/l |

This feed solution was maintained in such a fashion that the residual glucose in the fermentor ranged from 2–5 g/l. After approximately 24 hr of feed, the biomass accumulated to 15–20 g/l, and was used to inoculate the pilot fermentor.

B. Medium preparation and sterilization: A 450-liter fermentor was filled to 190 liter with water containing Sigma corn steep liquor (600 g–3.0 g/l) and MAZU 204 antifoam (10 ml–0.05 ml/l). This solution was sterilized for 60 minutes at 121° C., and then cooled to 36° C. The following components were then added to 5 liters (final volume) of water, and the total contents aseptically added to the fermentor through a Millidisk sterile filter.

| Medium Component | Total Added | Final Concentration |
|---|---|---|
| Potassium Hydroxide (87.5%) | 348 g | 1.83 g/l |
| Phosphoric Acid (85%) | 625 g | 3.29 g/l |
| (NH$_4$)$_2$SO$_4$ | 523 g | 2.75 g/l |
| MgSO$_4$·7H$_2$O | 211 g | 1.11 g/l |
| Trace metal 8 solution | 950 ml | 5.0 ml/l |

The volume of the fermentor was adjusted to 200 liters with sterile water, and the pH adjusted to pH 6.0 with anhydrous ammonia.

C. Fed-batch fermentation phase: At this point, the entire contents of the 14-liter inoculum vessel were aseptically transferred to the 450-liter fermentor. When the residual glucose level in the fermentor decreased to 5 g/l (in approximately 12–15 hr), nutrient addition to the fermentor commenced. Two sterile nutrient feed streams were aseptically added to the fermentor in a 1:1 ratio such that the residual glucose was maintained at 3.5 g/l during this "fed-batch" portion of the fermentation. The two nutrient feed streams are listed below.

| Feed Solution #1 | Feed Solution #2 |
|---|---|
| Glucose (600 g/l) | Phosphoric acid (61 g/l) |
| FeSO$_4$·7H$_2$O (0.6 g/l) | Potassium hydroxide (34 g/l) |
| Citric acid (1.2 g/l) | Trace metal 8 solution (96 ml/l) |
| | NH$_4$NO$_3$ (42 g/l) |

During this period of nutrient feeding, the pH was controlled at pH 6.0±0.2 by the addition of anhydrous ammonia, and the dissolved oxygen was maintained at greater than 40% of saturation. After approximately 15 hr of nutrient feed, the biomass accumulated to 25–30 g/l, and the continuous phase of carotenoid production was initiated.

D. Continuous fermentation phase: The continuous phase is characterized by allowing the glucose addition rate to become growth limiting, and by maintaining a fixed dilution rate once the desired dilution rate is achieved. In the present example, the target dilution rate was 0,045 hr$^{-1}$.

As in the fed-batch portion of the fermentation, the nutrient feed consisted of two different sterile feed streams, and the composition of these streams is shown below. In this case, however, the ratio of the glucose feed to the salts feed was maintained at 1:3.9.

| Feed Solution #1 | Feed Solution #2 |
|---|---|
| Cerelose (600 g/l) | Phosphoric acid (6.1 g/l) |
| FeSO$_4$·7H$_2$O (0.6 g/l) | KOH (34 g/l) |
| Citric acid (12 g/l) | MgSO$_4$·7H$_2$O (47 g/l) |

-continued

| Feed Solution #1 | Feed Solution #2 |
|---|---|
| | Trace metal 8 solution (9.6 ml/l) |
| | NH$_4$NO$_3$ (4.2 g/l) |

In the present example, the combined nutrient feed was initiated to give a dilution rate of 0.045 hr$^{-1}$. The dilution rate was then maintained at this level for approximately 80 hr of continuous operation. During this continuous fermentation phase, the carotenoid level of the biomass averaged 0.53%. Approximately 40% of the total carotenoids were zeaxanthin. Thus, in this fermentation, *N. excentricum* ATCC No. 74108 (also called HZ1236/274) produced, on the average, about 2.1 mg zeaxanthin per gram dry cell weight. The cumulative volumetric productivity for the run described was 3.9 mg xanthophyll per liter-hr.

EXAMPLE 6

Poultry Feeding Trial

A poultry feeding trial compared the pigment enhancement capabilities of *N. excentricum* ATCC No. 74108 (also called HZ1236/274)zeaxanthin-containing biomass powder (BioZea), *N. excentricum* ATCC No. 40335 xanthophyll-containing biomass powder (BioXan), and a marigold-based xanthophyll extract (Chromophyll-Oro).

*N. excentricum* ATCC No. 74108 (also called HZ1236/274) and *N. excentricum* ATCC No. 40335 were cultured as described in Examples 4 and 5. BioZea was prepared by separating zeaxanthin-producing microorganisms from the fermentation medium by centrifugation and spray drying the biomass to obtain zeaxanthin-containing biomass powder BioZea with a 3–5% moisture content. BioZea contained about 7 mg xanthophyll per gram dry cell weight, of which about 50% was zeaxanthin. BioXan was prepared in a similar manner except the biomass was not washed prior to spray drying. BioXan contained about 7 mg xanthophyll per gram dry cell weight, of which about 2–4% was zeaxanthin. Chromophyll-Oro was obtained from Laboratorios Bioquimex, S.A. The amounts of BioZea, BioXan, and Chromophyll-Oro used in the trial were standardized based on total xanthophyll content. A total of 640 12-day old male, commercial broiler chickens of the species *Gallus domesticus* were split into 10 treatment groups and for 18 days were fed one of the following amounts of xanthophyll per ton (t) of poultry feed: (1) none; (2) 10 g/t BioZea; (3) 20 g/t BioZea; (4) 40 g/t BioZea; (5) 10 g/t BioXan; (6) 20 g/t BioXan; (7) 40 g/t BioXan; (8) 10 g/t Chromophyll-Oro; (9) 20 g/t Chromophyll-Oro; a Chromophyll-Oro. The composition of poultry feed is shown in Table I.

TABLE I

| Poultry Feed Formulation and Nutrient Specifications | |
|---|---|
| Ingredient | Percent |
| Milo, ground | 61.15 |
| Soybean Meal - 47.5% | 25.77 |
| Fat:Blend - 3800 | 5.87 |
| Meat and Bone Meal - 50% | 5.13 |
| Phosphate/Defluor. | .72 |
| Limestone | .44 |
| Salt | .33 |
| DL-Methionine 99% | .25 |
| Broiler Vitamin Premix | .15 |
| Coban | .11 |
| Trace Mineral Premix | .05 |
| L-Lysine HCL 98% | .03 |

TABLE I-continued

| Poultry Feed Formulation and Nutrient Specifications | |
|---|---|
| Ingredient | Percent |
| | 100.00 |
| Protein | 20.31 |
| Fat | 8.05 |
| Fiber | 2.24 |
| Ca | 0.90 |
| Phos. available | 0.47 |
| Calories/Lb | 1464.64 |
| Xanthophyll, available | 0.00 |

Feed and water were supplied *ad libitum*. Birds were weighed at both the beginning and end of the study. At the end of the study, the flanks of the birds were evaluated for pigmentation using both Minolta Chroma Meter and Roche Color Fan tests, standard assays that measure the brightness, vividness, and hue of color samples. Results from the study are shown in Table II.

TABLE II

| Rank | Poultry Shank Pigmentation Scores | |
|---|---|---|
| | Treatment | |
| | | Minolta D.E. |
| 1 | 40 g/t BioZea | 50.62 |
| 2 | 40 g/t Chromophyll Oro | 45.54 |
| 3 | 40 g/t BioXan | 43.60 |
| 4 | 20 g/t BioZea | 41.13 |
| 5 | 20 g/t Chromophyll Oro | 38.15 |
| 6 | 20 g/t BioXan | 36.47 |
| 7 | 10 g/t Chromophyll Oro | 34.57 |
| 8 | 10 g/t BioZea | 34.37 |
| 9 | 10 g/t BioXan | 31.54 |
| 10 | Control | 26.46 |
| | | Roche Color Fan |
| 1 | 40 g/t BioZea | 5.11 |
| 2 | 40 g/t BioXan | 4.64 |
| 3 | 40 g/t Chromophyll Oro | 4.49 |
| 4 | 20 g/t BioZea | 4.22 |
| 5 | 20 g/t Chromophyll Oro | 3.75 |
| 6 | 20 g/t BioXan | 3.58 |
| 7 | 10 g/t BioZea | 3.35 |
| 8 | 10 g/t Chromophyll Oro | 3.31 |
| 9 | 10 g/t BioXan | 3.00 |
| 10 | Control | 1.58 |

No differences were observed in feathering or fecal conditions among the treatment groups. As shown, chickens fed BioZea exhibited significantly more desirable pigmentation than did chickens fed either Chromophyll-Oro or BioXan indicating that BioZea is a preferred pigment enhancer for poultry.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A zeaxanthin-producing algal microorganism selected from the group consisting of a microorganism having all of the identifying characteristics of *Neospongiococcum excentricum* HZ 1236/274, ATCC No. 74108; HZ 1236/437, ATCC No. 74109: HZ 1236/538, ATCC No. 74107, and a mutant thereof, wherein said mutant is capable of producing at least about 1.75 mg zeaxanthin per gram dry cell weight.

2. A zeaxanthin-containing formulation comprising a mutated algal microorganism which is selected from the group consisting of a microorganism having all of the identifying characteristics of *Neospongiococcum excentricum* HZ 1236/274, ATCC No. 74108; HZ 1236/437, ATCC No. 74109; HZ 1236/538. ATCC No. 74107, and a mutant thereof, wherein said mutant is capable of producing at least about 1.75 mg zeaxanthin per gram dry cell weight.

* * * * *